(12) United States Patent
Wang et al.

(10) Patent No.: US 6,318,151 B1
(45) Date of Patent: Nov. 20, 2001

(54) SELF-CONTAINED STERILANT MONITORING ASSEMBLY AND METHOD OF USING SAME

(75) Inventors: Jianjun Wang; David A. Mondiek, both of Dublin, OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/360,772

(22) Filed: Jul. 26, 1999

(51) Int. Cl.$^7$ .................................................. G01N 25/00
(52) U.S. Cl. ............................................................ 73/25.01
(58) Field of Search ................................. 73/25.01, 31.06

(56) References Cited

U.S. PATENT DOCUMENTS

| | | | |
|---|---|---|---|
| 4,542,640 | * | 9/1985 | Clifford ...................................... 73/23 |
| 4,566,251 | * | 1/1986 | Spisak et al. ............................ 53/167 |
| 4,843,867 | * | 7/1989 | Cummings ................................. 73/23 |
| 5,432,500 | * | 7/1995 | Scripps .................................. 340/628 |
| 5,491,092 | * | 2/1996 | Colvin ........................................ 436/1 |
| 5,608,156 | * | 3/1997 | Ando et al. ........................... 73/31.06 |
| 5,801,010 | * | 9/1998 | Falkowski et al. ...................... 435/31 |
| 5,872,359 | * | 2/1999 | Stewart et al. .................. 250/339.12 |
| 5,882,590 | | 3/1999 | Stewart et al. . |
| 6,002,340 | * | 12/1999 | Smith .............................. 340/825.06 |
| 6,063,631 | * | 5/2000 | Ignacio ...................................... 436/1 |
| 6,078,269 | * | 6/2000 | Markwell et al. ................ 340/825.5 |
| 6,085,576 | * | 7/2000 | Sunshine et al. .................... 73/29.01 |
| 6,161,259 | * | 12/2000 | Rabenecker ........................... 24/3.11 |
| 6,189,368 | * | 2/2001 | Ichida et al. ......................... 73/31.06 |

FOREIGN PATENT DOCUMENTS

| | | |
|---|---|---|
| 2603777 | 3/1988 | (FR) . |
| WO 9833286 | 7/1998 | (WO) . |

OTHER PUBLICATIONS

NASA Tech Briefs, vol. 14(6): 106 (Jun. 1990).
J. Dietschmann, "Hydrogen Peroxide in the Inhaled Air-Monitoring and Plant Optimization Using Sensor Technology", *450 Flüssiges Obst (Liquid Fruit)*, vol. 63: 450–453 (Aug. 1996) (Including translation).

"A New $H_2O_2$ Measurement and Control System", *Food Marketing & Technology*: 41 (Feb. 1997).

I. Taizo et al., "Application of a Newly Developed Hydrogen Peroxide Vapor Phase Sensor to HPV Sterilizer", *PDA Journal of Pharmaceutical Science & Technology*, vol. 52 (1): 13–18 (1998).

* cited by examiner

*Primary Examiner*—Helen Kwok
*Assistant Examiner*—Charles D. Garber
(74) *Attorney, Agent, or Firm*—David L. Weinstein; Brian R. Woodworth (57) ABSTRACT

A system for monitoring concentrations of sterilant, such as hydrogen peroxide vapor, within a sterilization apparatus, includes a self-contained, sterilant monitoring assembly that is freely positionable within the sterilization apparatus. The assembly includes a gas-detecting sensor and associated temperature sensor mounted on a portable structure, as well as a suitable data collection circuit for receiving output signals from the sensors. The assembly also includes signals connectors, such as a physical data port or a remote transmitter, or both. Signals can be transmitted concurrently with data collection, or an electronic memory may be provided for subsequent transfer of the collected data. Collected data is transferred to a remote communication unit positioned exteriorly of the sterilization apparatus. The collected data is processed by a processor, which is either provided as part of the monitoring assembly or provided remotely as part of the monitoring system as a whole, to identify the corresponding detected sterilant levels. The assembly is operated by a power source, which can be activated manually, by preprogrammed relays, or remotely by a control system capable of receiving control signals via near infrared or radio wave transmissions. A carrier element is provided to carry the sterilant monitoring assembly along the conveyor path of the sterilization apparatus and, thus, collect data at each sterilization station.

8 Claims, 5 Drawing Sheets

SELF-CONTAINED STERILANT MONITORING ASSEMBLY AND METHOD OF USING SAME

FIELD OF THE INVENTION

The present invention relates generally to a system for monitoring levels of a sterilant during a sterilization process, and more particularly to a self-contained monitoring assembly configured to monitor hydrogen peroxide ($H_2O_2$) vapor levels during sterilization of articles such as packages, vessels, machines or the like.

BACKGROUND OF THE INVENTION

Aseptic processing of consumable goods, such as nutritional compounds and food products, is typically effected by separate sterilization of the contents and the containers within which the contents are packaged. Subsequent to separate sterilization, the contents are placed in the containers and sealed in a sterile environment for shipment, storage and use.

Sterilization of such containers prior to contacting the desired sterilized contents can be performed efficiently by use of a sterilant such as hydrogen peroxide ($H_2O_2$) vapor. In such a process, the containers are introduced into a sterilization apparatus in which the containers are flushed with hydrogen peroxide vapor. The containers are subsequently flushed with warm air or any other fluid suitable to achieve desirably low levels of residual hydrogen peroxide. This general procedure is highly effective in achieving sterilization of the containers, and likewise can be performed on any other suitable articles that will come into contact with the desired compound.

Notwithstanding the effectiveness of hydrogen peroxide ($H_2O_2$) sterilization, accurate monitoring of $H_2O_2$ vapor concentration levels can be problematic. This is due in part to the physical and chemical property changes of hydrogen peroxide vapor under processing conditions, and further due to decomposition upon contact with surfaces of various materials within the processing area. As such, undesired deviation of hydrogen peroxide vapor concentration, and excessive decomposition, can result in loss of sterility of the containers and surrounding aseptic processing area. By contrast, hydrogen peroxide vapor is corrosive in nature, and thus excessive concentration levels can result in detrimental effects to the surrounding equipment and surfaces. Furthermore, and in accordance with government standards, low residual sterilant levels must be maintained for subsequent use of the sterilized containers.

Heretofore, hydrogen peroxide vapor detection systems have been undesirably bulky, as exemplified by conventional near infrared (NIR) analysis apparatus. Additionally, known off-line testing is typically too slow to monitor sterilant levels with sufficient accuracy. Previous arrangements have not provided "real time" monitoring throughout an aseptic processing cycle, and particularly have not been capable of monitoring hydrogen peroxide vapor concentrations within a container or like article as it is sterilized.

The present sterilant monitoring system, and the self-contained assembly thereof, overcomes these deficiencies in the prior art by providing a highly accurate, cost effective arrangement for providing real-time monitoring of a sterilant, such as hydrogen peroxide vapor, and is configured to facilitate monitoring of the sterilant levels throughout the processing cycle of a sterilization apparatus.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied and broadly described, the invention includes a sterilant monitoring system particularly suited for monitoring concentrations of a sterilant, such as hydrogen peroxide ($H_2O_2$) vapor, as used by a sterilization apparatus. The system includes a self-contained monitoring assembly that can be readily positioned proximate the sterilization apparatus. It is particularly contemplated that the monitoring assembly be positioned within a carrier element configured as one of the articles to be sterilized by the sterilization apparatus. In this manner, the sensor structure can be moved through the sterilization apparatus so as to monitor sterilant concentration levels throughout a processing cycle.

In accordance with the illustrated embodiment, the present sterilant monitoring system is particularly configured for a sterilization apparatus using a sterilant such as hydrogen peroxide vapor. Further in accordance with the invention, and as embodied herein, the system uses a sterilant monitoring assembly for data collection purposes. The sterilant monitoring assembly includes a sterilant sensor configured to provide output signals corresponding to detected levels of the sterilant. The sterilant sensor preferably includes a gas-detecting semi-conductor element, and a heating element operatively associated therewith to elevate the temperature of the gas-detecting semi-conductor element to an appropriate operating temperature. A data collection circuit is operatively coupled to the sterilant sensor to receive the output signals from the sensor as collected data, with the assembly including a power source to provide electrical power to the sensor and the data collection circuit as needed. In the preferred form, a temperature sensor also is operatively connected to the data collection circuit to provide output signals corresponding to the ambient temperature proximate the sterilant sensor for collection in combination with the output signals from the sterilant sensor. In this manner, the temperature data may be used as a reference to correlate more accurately the sensor output signals with corresponding $H_2O_2$ vapor concentration levels.

The sterilant monitoring assembly of the present invention is configured as a self-contained, portable unit. That is, the sterilant sensor, data collection circuit, and power source, as well as the preferred temperature sensor, are self-contained on a portable structure so as to be freely positionable proximate the sterilization apparatus to monitor levels of sterilant thereat. In a preferred form, the portable structure is mounted on a carrier element configured as an article to be sterilized by the sterilization apparatus, such as a container or like article.

In accordance with the invention, collected data can be processed by configuring the monitoring system as a whole, and the data collection circuit particularly, in any of a variety of different arrangements. In one arrangement of the invention, the data collection circuit includes an electronic memory to create a readable memory of the data collected during a selected time interval. The assembly of this arrangement may include a signal connector, such as data port or a transmitter, to allow transfer of signals representative of the collected data from the electronic memory to a remote communication unit that is joined in communication with the signal connector. In this manner, the collected data can be transferred or downloaded to a processor, which forms a part of the sterilant monitoring system as a whole. Once downloaded, the collected data can thereafter be stored, graphically displayed in various forms, or otherwise analyzed and processed to identify and monitor the detected sterilant concentration levels.

Alternatively, or additionally, the monitoring assembly may be configured to transmit remotely the collected data simultaneous with collection to a remote communication unit positioned exteriorly of the sterilization apparatus. In this configuration, the data collection circuit of the monitoring assembly preferably includes a transmitter to transmit signals representative of the collected data to a remote communication unit. Radio frequency or near infrared transmission are presently preferred for such remote transmission. If desired, an electronic memory and physical signal connector also may be provided in combination with the transmitter for back-up purposes.

As will be appreciated, sterilization processing typically entails the passage of articles through a sterilization apparatus, with attendant variations in temperature and sterilant concentrations during the process. It is desirable to collect data corresponding to selected intervals or conditions during the processing cycle. The present monitoring assembly therefore may also include a circuit to select certain conditions, such as time or temperature, for data collection, and a signal connector or a control device to allow entry of such selected conditions.

In order to effect data collection in a manner that accurately corresponds to the processing conditions to which articles are subjected by the sterilization apparatus, the present monitoring system preferably includes a carrier element for mounting the self-contained portable structure of the monitoring assembly thereon. Preferably, the carrier element is configured as an article similar to that to be sterilized by the apparatus. In the illustrated embodiment, this carrier element is configured as a container having a shape and dimensions essentially the same as containers normally sterilized in the apparatus. Notably, the carrier element is configured such that the portable structure can be positioned inside the carrier element, thus providing data collection corresponding to conditions within a container during the sterilization process.

Other features and advantages of the present invention will become readily apparent from the following detailed description, the accompanying drawings, and the appended claims.

The accompanying drawings, which are incorporated in and constitute part of this specification, are included to illustrate and provide a further understanding of the method and system of the invention. Together with the description, the drawings serve to explain the principles of the invention.

DETAILED DESCRIPTION OF THE PREFERRED EMBODIMENT

Reference will now be made in detail to the present preferred embodiments of the invention, an example of which is illustrated in the accompanying drawings. The method and corresponding steps of the invention will be described in conjunction with the detailed description of the system and assembly.

While the present invention is susceptible of embodiment in various forms, there is shown in the drawings and will hereinafter be described presently preferred embodiments, with the understanding that the present disclosure is to be considered as an exemplification of the invention, and is not intended to limit the invention to the specific embodiments illustrated.

Figure 1:
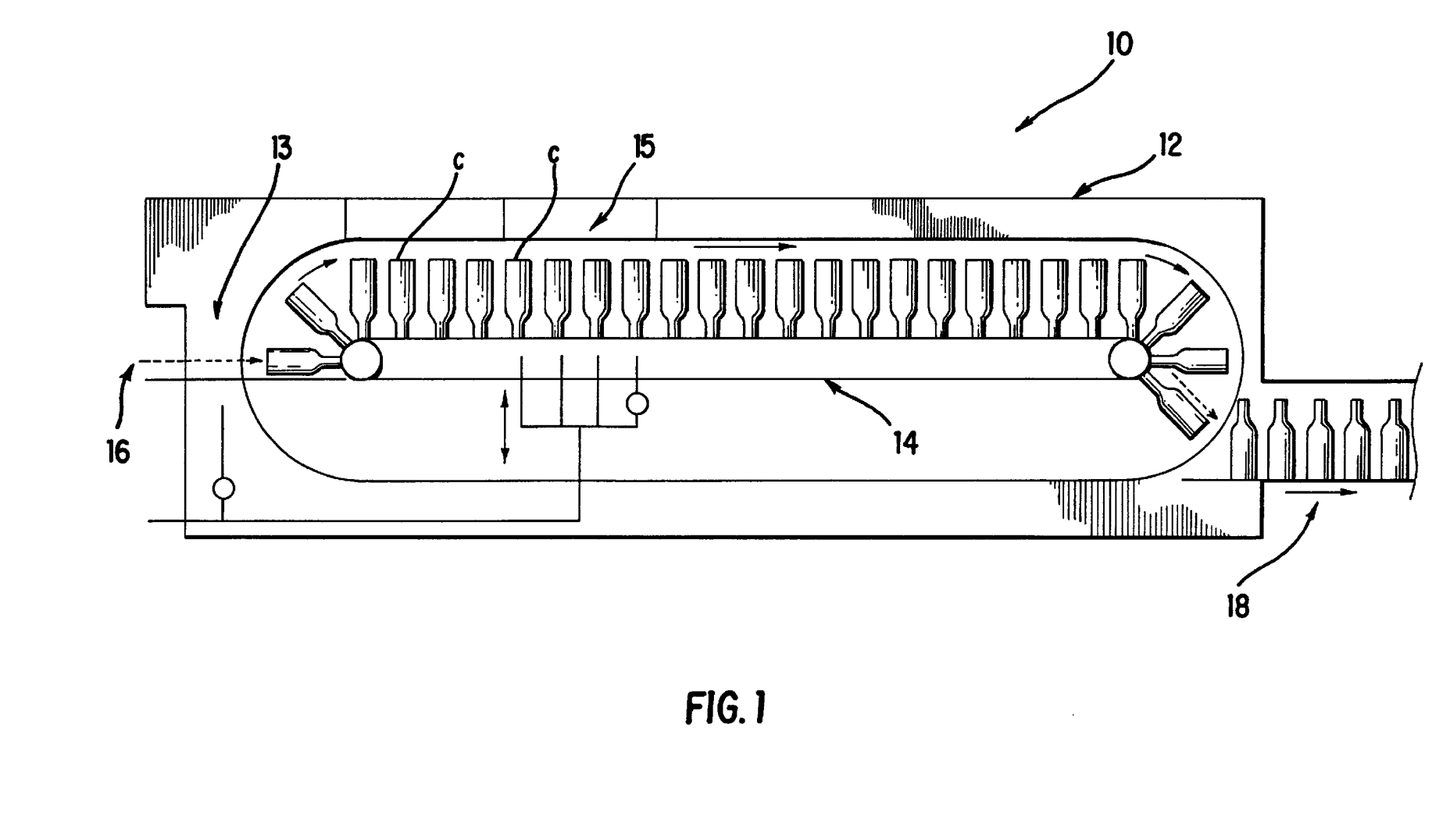
FIG. 1 is a diagrammatic view of a sterilization apparatus of a type for which the present sterilant monitoring system is suited.

FIG. 1 diagrammatically illustrates a sterilization apparatus 10 of the type used for effecting sterilization of containers C, such as packages, vessels or like articles. This representative sterilization apparatus typically effects sterilization of the containers C by exposing portions of the interior and exterior of each container to a sterilant, such as hydrogen peroxide ($H_2O_2$) vapor. The containers C are processed in this fashion for subsequent filling with sterile contents, thus completing aseptic processing and packaging of the contents. The contents may include any of a variety of consumable products including, but not limited to, nutritional and therapeutic compounds, as well as food products or beverages.

The sterilization apparatus 10 includes an enclosure 12 within which an article conveyor 14 operates for movement of containers C or other like articles to be sterilized along a conveyor path through the apparatus. The containers C are typically introduced into the apparatus at a product infeed station, generally designated by reference character 16. The containers C are then received by the conveyor 14 for movement through the apparatus 10, and subsequently discharged after sterilization at container discharge 18. As the containers C are moved through the apparatus 10, both the interior and exterior of each container C is subjected to sterilizing contact with an appropriate sterilant. A variety of know sterilants are available, such as ethylene oxide, although hydrogen peroxide vapor is preferred. In the representative embodiment of the sterilization apparatus, the exterior of each container is fogged with the sterilant at an appropriate station 13 along the conveyor path. The apparatus 10 also includes suitable probe-like elements at a subsequent station 15 for introducing a hydrogen peroxide vapor fog into the interior of each container C. The sterilization apparatus also may include pre-warming and drying stations along the conveyor path as needed for efficient sterilization and effective removal of any sterilant residue prior to filling the containers C with the desired contents. Such sterilization apparatus are known and available from a variety of sources, such as Robert Bosch GmbH.

As previously noted, it is desirable to monitor sterilant levels within the sterilization apparatus 10. Often, however, and particularly when $H_2O_2$ vapor is used as the sterilant, monitoring can be difficult. For example, hydrogen peroxide vapor is subject to decomposition and oxidation, and thus can be difficult to monitor accurately due to its unstable and corrosive nature. While it is desirable to monitor the various stations within the apparatus 10, the hydrogen peroxide vapor itself is a very strong oxidizing agent, and thus excessive levels of hydrogen peroxide vapor within the sterilization apparatus 10 complicate maintenance and operation of certain permanently mounted sensors. Furthermore, it can be particularly desirable to monitor sterilant levels actually within the containers C being moved through the apparatus 10 for greater accuracy. Heretofore, however, such precise monitoring has not been possible.

Figure 4:
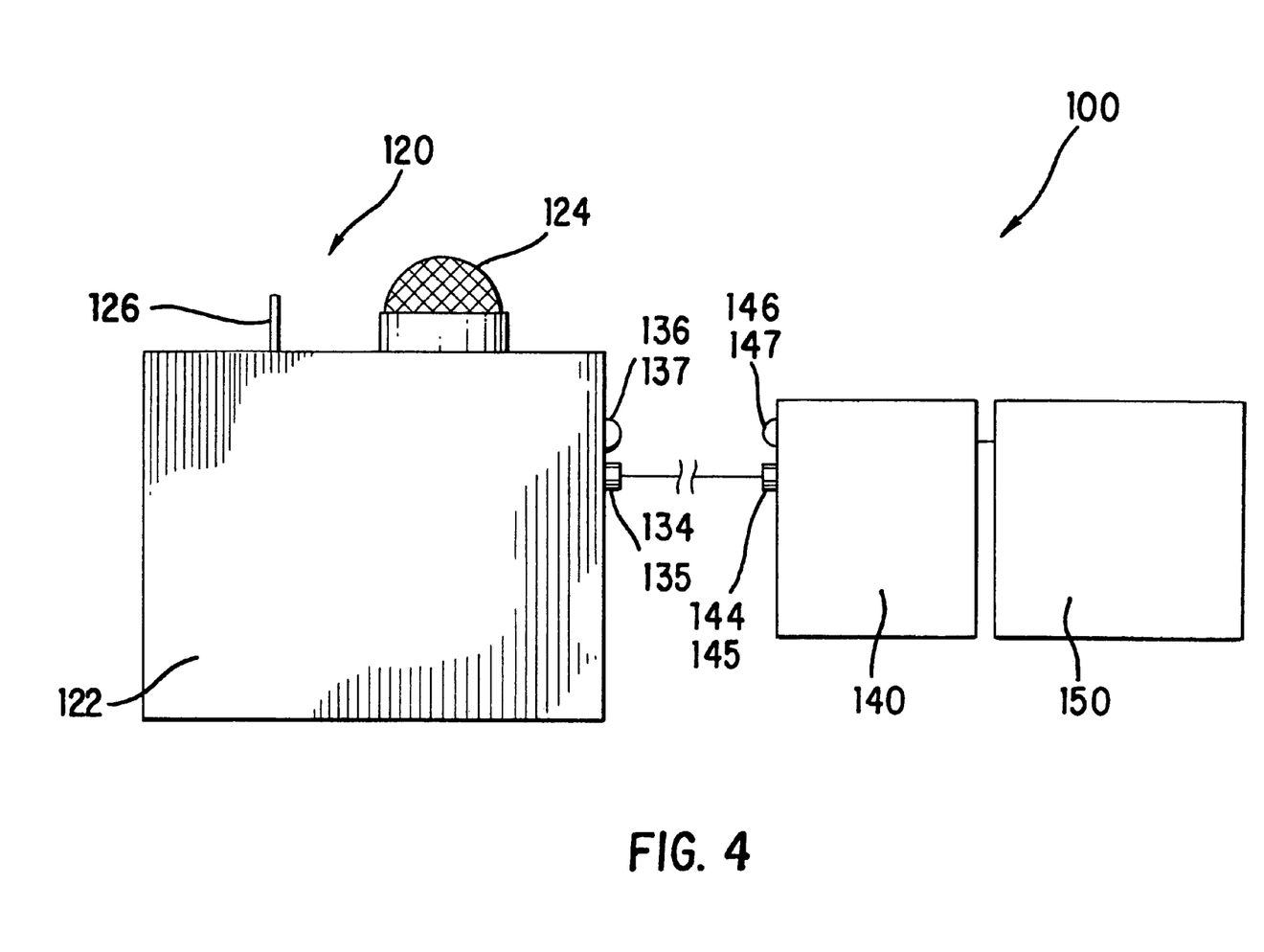
FIG. 4 is a diagrammatic side view of the present monitoring system, including the monitoring assembly of the system, and an associated remote communication unit to which data collected by the sensor structure is transmitted.

In accordance with the present invention, a sterilant monitoring system is provided for the sterilization apparatus, with the monitoring system particularly suited for monitoring concentrations of hydrogen peroxide vapor within the apparatus. The present monitoring system, which is generally designated by reference character 100 as shown in FIG. 4, includes a sterilant monitoring assembly 120. In accordance with the invention, the monitoring assembly 120 is self-contained on a portable structure for disposition within the sterilization apparatus 10. As will be further described, the sterilant monitoring assembly 120 is configured to collect data from within the sterilization apparatus 10, and to permit analysis of the collected data either by an onboard processor chip or by its transfer to a remote processor 150, which forms part of the sterilant monitoring system 100 as a whole. The present monitoring system 100 therefore further includes a remote communication unit 140, preferably positioned exteriorly of the sterilization apparatus 10 to receive and communicate signals to the processor 150. The remote communication unit 140 is configured to receive data from the sterilant monitoring assembly 120 by a signal connector; either by a physical connection, such as a data port 134 or by a wireless transmitter 136, such as by radio frequency or near infrared transmission.

Notably, the monitoring assembly 120 is sized and configured to be positioned proximate the sterilization apparatus 10, such as within a desired chamber or cavity of the sterilization apparatus 10. Preferably, however, the sterilant monitoring assembly 120 is configured to be positioned on a carrier element 160 having a shape and size similar to that of an article to be sterilized (e.g., a bottle or container). The sterilant monitoring assembly is thus optimally positioned to monitor sterilant concentrations within the sterilization apparatus 10 throughout a sterilization cycle.

The sterilant monitoring assembly 120 includes a portable structure 122, which may be in the form of a base member, or, more preferably, as an outer housing capable of self-containing the various components of the sterilant monitoring assembly 120. Preferably, the external housing 122 is constructed of suitable corrosion-resistant material so as to withstand the effects of repeated exposure to hydrogen peroxide vapor. Examples of such corrosion-resistant material include stainless steel and certain plastic or synthetic materials, although Teflon is preferred. Depending upon the material selected, the portable structure 122 can be electrically conductive, such that the portable structure 122 may be employed as an electrical contact for transmission of collected data via a hard-wire connection as will be described.

Figure 2:
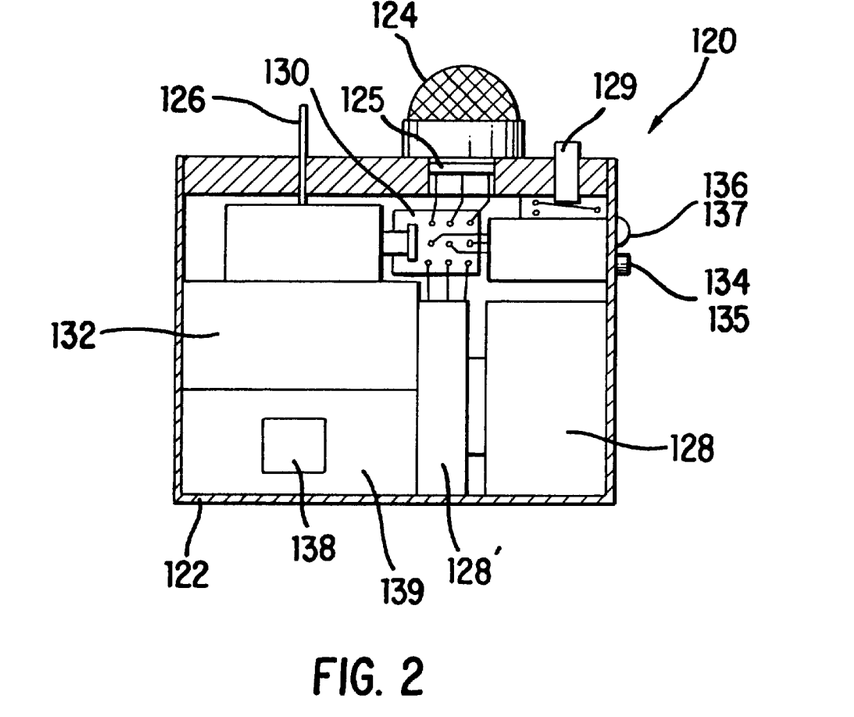
FIG. 2 is a diagrammatic cross-sectional side view of a representative embodiment of the sterilant monitoring assembly of the present invention.
Figure 3:
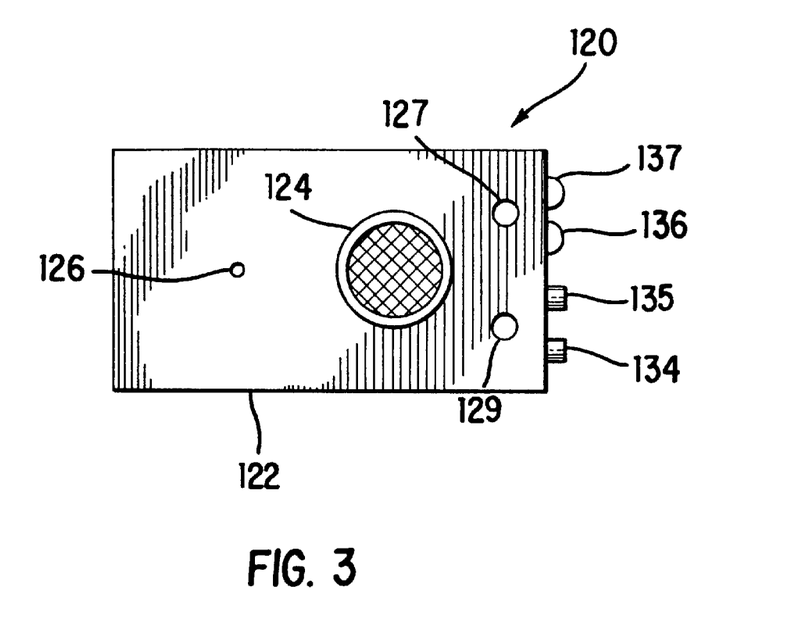
FIG. 3 is a diagrammatic, top plan view of the sterilant monitoring assembly shown in FIG. 2.

In accordance with the present invention, the sterilant monitoring assembly includes a sterilant sensor to provide output signals corresponding to detected levels of the sterilant. As embodied herein, and as shown in FIGS. 2–4 the sensor 124 includes a commercially available gas-detecting sensor, preferably of the type which employs a semi-conductor sensing element 125. This sensing element 125 generally includes a metal dioxide (such as tin dioxide), which is sintered to form a film on the surface of an associated ceramic tube (such as alumina ceramic). A heating element, such as a resistance heating coil, is positioned within the ceramic tube to elevate the temperature of the gas-detecting semi-conductor element up to about 400° C. When the sensing element 125 is exposed to sterilant $H_2O_2$ vapor, the metal dioxide surface absorbs the vapor molecules and causes oxidation. In this manner, it has been found that electrical resistance is reduced and, thus, the output signal generated by the sensor 124 increases proportionally with increasing vapor concentration level. In an illustrative preferred embodiment of the present sterilant monitoring assembly for use with hydrogen peroxide vapor sterilant, a Model 816 sensor from FIGARO U.S.A., Inc., of Glenview, Ill., is employed as the sterilant sensor to detect $H_2O_2$ vapor concentration levels. Alternative sensor configurations capable of performing the similar function as described likewise may be used if desired and suitable.

In accordance with an additional aspect of the invention, it is desirable for the sterilant monitoring assembly 120 to include a temperature sensor 126, such as a thermistor or the like, to provide output signals corresponding to the ambient temperature proximate the sterilant sensor 124. A variety of conventional temperature sensors are known and may be adapted for use with the monitoring assembly of the present invention. The illustrative sterilant monitoring assembly embodied herein, for example, includes an FRB Pressure Micropack available from DATATRACE, Inc. of Lakewood, Colo., which has been modified to accommodate the FIGARO Model 816 sensor in place of a conventional pressure sensor. Because sterilant concentration levels are affected by the ambient temperature, the output signals from the temperature sensor 126, if provided, are used to correlate more accurately the output signals from the sterilant sensor 124 with the proper corresponding sterilant concentration levels. This function can be performed either by an on-board processor chip, if provided, or by the processor 150 of the sterilant monitoring system 100, as will be described. If desired, pressure, relative humidity or other parameter sensors may be provided in addition to or in place of the temperature sensor 126 to obtain corresponding data respectively.

Further in accordance with the invention, a data collection circuit 130 is operatively coupled to the sterilant sensor 124 to receive the output signals from the sterilant sensor 124 as collected data. FIG. 2 shows that the data collection circuit 130 also is operatively coupled to receive output signals from any additional sensors that are provided, such as the temperature sensor 126 to provide signals corresponding to ambient temperature proximate the sterilant sensor 124. The data collection circuit 130 may be provided as a conventional hard wire assembly or, as in the preferred embodiment, be configured to include a chip or printed circuit in a known manner for reduced size and increased capacity. As described further below, the data collection circuit may include a memory chip to store entered data, a central processing unit (CPU) configured to control select functions, as well as programmable solid state relays for operation of the sterilant monitoring assembly.

As previously noted, the sterilant monitoring assembly 120 of the present invention is self-contained on a portable structure. The sterilant monitoring system therefore includes a power source 128 for the various electrically driven components, such as the sterilant sensor 124, the temperature sensor 126, the data collection circuit 130 and any additional components provided as needed. Any of a variety of known power sources may be used depending on its desired characteristics, such as size, weight, and capacity. In the preferred embodiment herein, a conventional DC lithium battery is provided. Additionally, the power source 128 will include a converter and/or transformer if necessary to provide the appropriate power to each of the various components of the sterilant monitoring assembly 120. For example, the illustrative embodiment disclosed herein includes a DC/DC converter 128' to covert a 9 volt supply into the appropriate voltage requirements for the components of the assembly 120. A light-emitting diode (LED) indicator 127 is provided to indicate activation of the power source 128. The power source 128, and associated components, are provided in the portable structure and, therefore, should be of suitable size.

An additional aspect of the invention involves the transmission of the collected data from the various sensors of the sterilant monitoring assembly 120 to the processor 150 of the sterilant monitoring system 100. FIG. 4 diagrammatically illustrates the components of the present sterilant monitoring system which cooperate with the sterilant monitoring assembly 120 to transfer and process the collected data. The sterilant monitoring system includes a remote communication unit 140 which can be operatively coupled in any of a variety of configurations with the sterilant monitoring assembly 120 and further is in operative communication with the processor 150. Data transfer may be performed via a physical connection between the sterilant monitoring assembly 120 and the remote communication unit 140, or via a transmitter for wireless transmission, or both as shown in FIG. 4.

To perform data transfer via a physical connection, the data collection circuit 130 of the sterilant monitoring assembly 120 preferably includes an electronic memory 132, such as a suitable chip or a circuit, to create a readable memory of the collected data during a selected time interval. For example, a suitable electronic memory 132 for the illustrative assembly embodied herein is incorporated using an FRB Pressure Micropack having an increased memory capacity from DATATRACE, Inc., as modified to accommodate the FIGARO sensor.

Once data collection is complete, transfer of the collected data that is stored in the electronic memory 132 can be performed. This is accomplished by providing the sterilant monitoring assembly 120 of this embodiment with a signal connector, such as a data port 134 for physical connection with a data port 145 on the remote communication unit 140, to permit transfer of signals representative of the collected data from the electronic memory 132. Use of this system configuration thereby allows transfer of the collected data via a physical connection to the remote communication unit 140. If desired, the collected data from the electronic memory 132 can be transmitted remotely via a transmitter 136 to the remote communication unit 140 as described further below.

Alternatively, or in addition to the delayed transfer of collected data using a physical connector, such transfer can be effected simultaneously with data collection by including a transmitter 136 as the signal connector. The transmitter 136 transmits signals representative of the collected data via a wireless connection, such as by radio frequency or near infrared, to a receiving element 147 of the remote communication unit 140 during the selected interval of operation. It thus can be appreciated that the sterilant monitoring assembly 120 and remote communication unit 140 can be configured to provide "real time" transfer of collected data, thereby providing output signals representative of sterilant levels within sterilization apparatus 10 during an actual sterilization cycle. In this manner the electronic memory 132 is not necessary, although may still be provided if desired.

The interval for data collection can be selected simply by activating a power switch 129 connected to the power source 128, or through more sophisticated means. For example, the data collection circuit can be configured to collect data during selected conditions. Such selected conditions may include start time and stop time, or detected temperature or pressure conditions at which to activate or deactivate data collection. In this manner, a signal connector, such as a physical data port 135 or a receiver 137, is provided on the monitoring assembly 120 to receive signals from a corresponding data port 144 or transmitter 146 on the remote communication unit 140 to preprogram the selected conditions into the data collection circuit 130. Alternatively, it is possible for the power source to be programmed, such as by using programable relays or the CPU 132, to activate the sterilant sensor 124 at a certain time prior to data collection or in accordance with a preselected schedule.

Remote real time operations of the monitoring assembly 120 also can be accomplished, preferably by providing a near infrared or radio frequency control signal receiver or the like on the sterilant monitoring assembly 120 as part of the data collection circuit 130. In accordance with this aspect of the invention, and as embodied herein, a near infrared control system 138 and a programmable solid state relay circuit group 139 are provided for remote power activation of the monitoring assembly 120. A variety of such control systems and relay configurations are available. The presently preferred embodiment includes a NIKON ML-3 Modulite Remote Control Set F5/N90 from B&H Photo-Video of New York as modified appropriately in a conventional manner for operation of the sterilant monitoring assembly. For example, two transistor-transistor logic (TTL) compatible relays and a multicontact relay, each available from Philips ECG Products of Greeneville, Tenn., can be used to modify this control set. A normally opened relay (RLYF71A05) is provided to activate a multicontact miniature relay (RLY5140) for heating circuit power activation to latch the heating circuit, while a normally closed relay (RLYF71B05) is used to turn off the heating power and break the latch. Because the heating circuit is nearly 200 mA, it is beneficial to use a relay group and optocouplers to isolate the signals. Additionally, it is preferred that the heating circuit resistance remain constant; therefore, a mechanical contact is preferred.

By virtue of its self-contained, portable nature, the sterilant monitoring assembly 120 is freely positionable proximate the sterilization apparatus 10 to monitor levels of hydrogen peroxide vapor, or any other sterilant for which the sterilant sensor 124 is suited. If the collected data is to be recorded in the memory 132 of the monitoring assembly 120, and thereafter downloaded or transferred, the monitoring assembly can be positioned as desired within the sterilization apparatus 10, and subsequently removed for downloading of collected data. Alternatively, and if provided with the transmitter 136 to transmit collected data to the remote communication unit 140, the monitoring assembly 120 can be positioned proximate the sterilization apparatus 10, with transmission of collected data occurring subsequent to collection, or on a real-time basis. In this manner, the monitoring assembly 120 can be used to collect data related to sterilant concentration levels at select locations in or around the sterilization apparatus, or as a portable device to sample randomly and search for sterilant leaks if desired.

Figure 5:
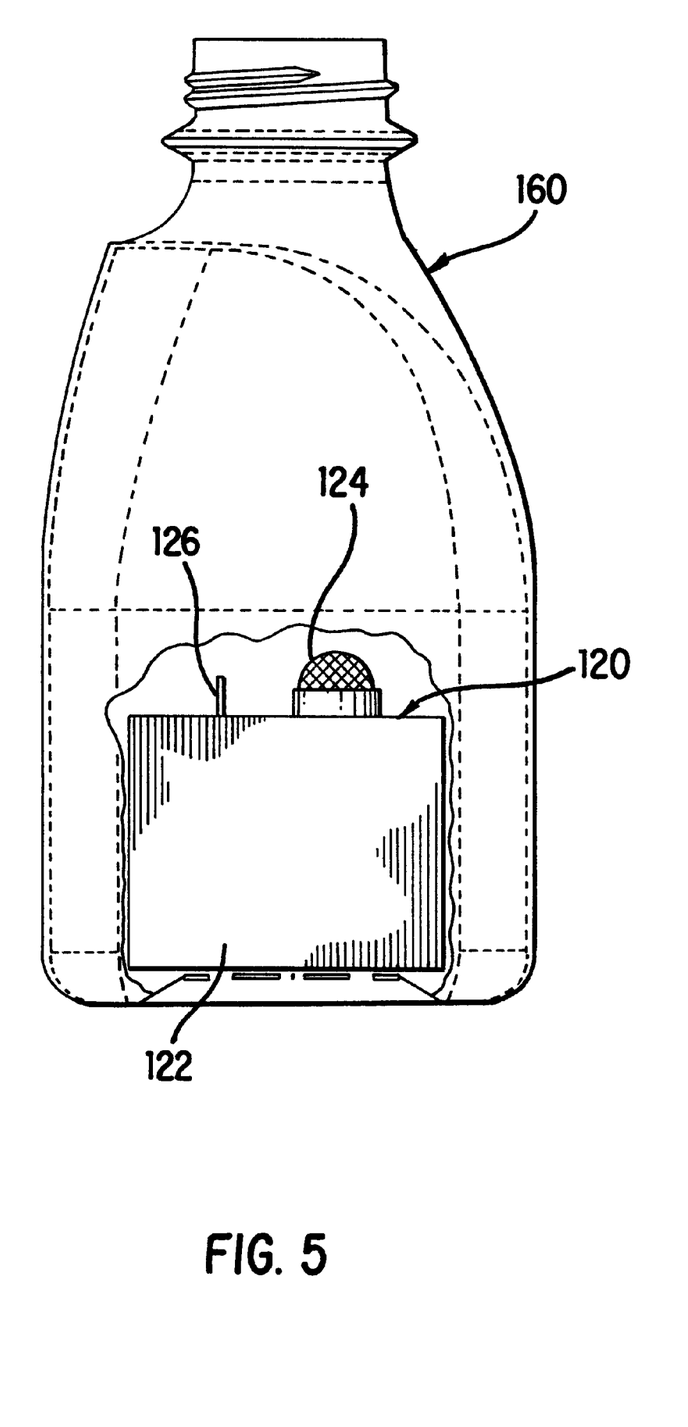
FIG. 5 is a partially fragmented side view illustrating the sterilant monitoring assembly of the present system in operative association with a carrier element configured as an article to be sterilized by the sterilization apparatus.

With reference to FIG. 5, a particularly preferred aspect of the present monitoring system is illustrated, wherein the monitoring assembly 120 is positioned in operative association with a carrier element 160 configured similar to an article (e.g., a container) to be sterilized by the apparatus 10. The monitoring assembly 120 is positionable on the carrier element 160 and, preferably, within the carrier element 160, to facilitate monitoring of sterilant levels at various stations of the sterilization apparatus 10. FIG. 5 illustrates the carrier element 160 including a fragmented portion illustrated in cutaway. While the carrier element 160 is shown in this form for purposes of illustration, it will be appreciated that the carrier element 160 may be provided with at least one removable portion, such as a removable side wall or removable bottom wall, to facilitate disposition and mounting of the sterilant monitoring assembly 120 within the carrier element 160. Because disposition of the portable sensor structure on the carrier element during sterilization by the sterilization apparatus 10 facilitates monitoring of the sterilization cycle to which the containers C are subjected, container C embodied herein is preferably configured to represent an actual container in all aspects to simulate real processing conditions.

Figure 6:
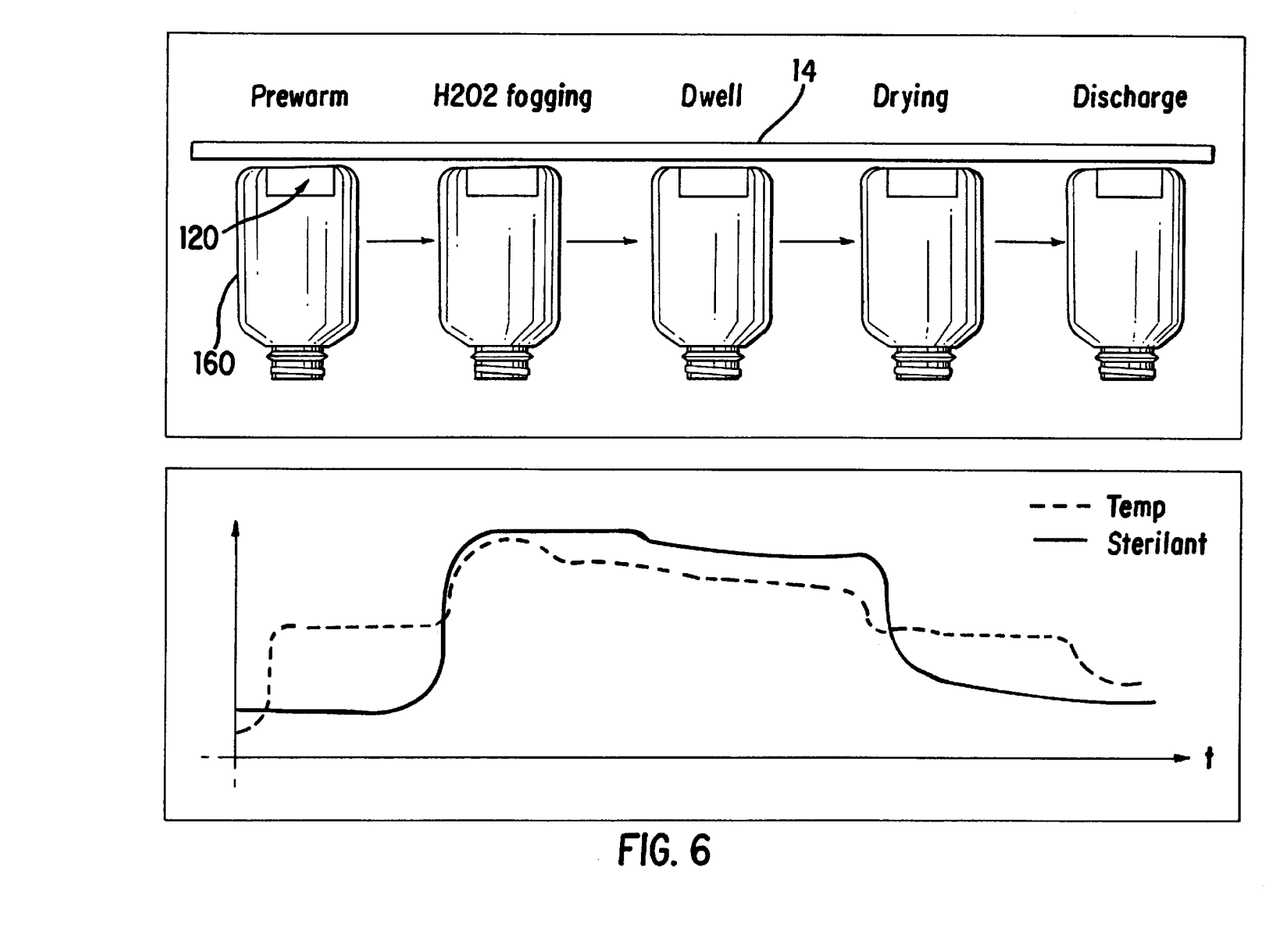
FIG. 6 is a schematic side view depicting the various stages of the processing cycle of the sterilization apparatus and the corresponding output signals collected by the sterilant monitoring assembly of the present invention.

Use of the present monitoring system will be apparent from the foregoing description, and is further illustrated by FIG. 6. The self-contained, portable sterilant monitoring assembly 120 is prepared for data collection, including selection of any conditions, such as time or temperature, that are required or desired for activation of the sensors and, if provided, the electronic memory and programable relays. The monitoring assembly 120 is positioned proximate the sterilization apparatus 10 to collect data representative of the sterilant levels thereat. While the monitoring assembly 120 may be simply positioned near or within the sterilization apparatus 10, it is particularly contemplated that the monitoring assembly 120 be moved along the conveyor path of the sterilization apparatus 10 by being placed first in the carrier element 160, and then loaded on the conveyor path defined by article conveyor 14 as shown schematically in FIG. 6.

The sterilant monitoring assembly 120 collects data representative of sterilant concentrations at each station of the sterilization apparatus 10. If the collected data is to be downloaded or transferred subsequent to removal of the monitoring assembly 120 from within the apparatus 10, the monitoring assembly 120 is provided with the readable electronic memory 132 from which collected data can be subsequently transferred to the remote communication unit 140 via signal connector 134, 136. Thus, use in this fashion contemplates that the monitoring assembly 120 is removed from within the sterilization apparatus 10 for transfer of the collected data. Transferred data includes not only output signals from the gas-detecting sensor 124, but also can include output signals collected from the temperature sensor 126 as shown in FIG. 6, or any other sensor that may be provided. The position of the structure within the apparatus 10 therefore can be traced by identifying the associated time and temperature. Alternatively, a separate timer or position tracer may be provided within monitoring assembly 120 if desired.

In the preferred embodiment, however, collected data is to be transferred from the monitoring assembly 120 without requiring removal of the monitoring assembly 120 from within the sterilization apparatus 10. The monitoring assembly 120 therefore is provided with a transmitter 136 to transmit signals representative of the collected data from the data collection circuit to the receiving element 147 of the remote communication unit 140. While the present monitoring system is particularly suited for detecting and monitoring sterilant levels within the sterilization apparatus 10, it will be appreciated that use of an arrangement including transmitter 136 ultimately can permit operation of the sterilization apparatus 10 itself by real-time monitoring of processing conditions within the apparatus 10 if desired.

Data collected by the monitoring assembly 120 and transferred via the remote communication unit 140, as illustratively represented in FIG. 6, is analyzed by the processor 150 to correlate the transferred signals into corresponding sterilant concentration levels using a known functional relation stored in the processor 150. This known relation can be programmed as a numeric formula, or established through the acquisition of sufficient experimental test data points at known test conditions. A variety of suitable remote communication units may be used, such as that of the THERMO•DOT system available from Stock America, Inc. of Milwaukee, Wis. Similarly, exemplary processors include any of a variety of personal computers and compatible data analysis software, such as that provided by DATATRACE, Inc. for use in conjunction with its sensors as modified to correlate the collected data with corresponding sterilant levels. Once processed, this information can be further analyzed, displayed, printed, or otherwise used as desired.

Alternatively, or additionally, the sterilant monitoring assembly 120 itself can include an on-board processor in the form of a chip or circuit to correlate the collected data into corresponding sterilant levels for subsequent storage in the memory 132 and/or for data transfer to the remote communication unit 140. The processor chip is preprogramed with the appropriate correlation using a known functional relation. As with the remote processor, this known relation can be programmed as a numeric formula, or established through the acquisition of sufficient experimental test data points at known test conditions. The processor chip or circuit is further configured to generate and transmit corresponding signals for storage or transfer. The processor chip can be formed integral with the data collection circuit, as embodied herein, or provided separately. An example of a suitable processor circuit includes the EPAC™ electrically programmable analog circuit, Model No. IMP50E10C, available from Digi-Key Corporation of Thief River Falls, Minn., as modified accordingly, although alternatives are available.

It will be apparent to those skilled in the art that various modifications and variations can be made in the method and system of the present invention without departing from the spirit or scope of the invention. Thus, it is intended that the present invention include modifications and variations that are within the scope of the appended claims and their equivalents. Furthermore, the technical descriptions provided regarding the theory of operation are for purpose of explanation and not limitation.

What is claimed is:

1. A method of monitoring levels of sterilant within a sterilization apparatus, the method comprising the steps of:
   providing a self-contained sterilant monitoring assembly including:
   a sterilant sensor configured to provide an output signal corresponding to detected levels of the sterilant,
   a data collection circuit operatively coupled to said sterilant sensor to receive the output signal from said sterilant sensor as collected data, and
   a power source to provide electrical power to said sterilant sensor and said data collection circuit, wherein the sterilant sensor, the data collection circuit and the power source are self-contained on a portable structure; and positioning said sterilant monitoring assembly proximate said sterilization apparatus to collect data representative of sterilant levels thereat; and transferring the collected data from the data collection circuit to a processor to identify the sterilant levels detected by the sterilant sensor, wherein said sterilization apparatus sterilizes articles moved along a conveyor path, said positioning step including moving said sterilant monitoring assembly along said conveyor path.

2. A method of monitoring sterilant in accordance with claim 1, wherein:

the data collection circuit of the sterilant monitoring assembly provided by the providing step further includes an electronic memory to create a readable memory of the data collected during a selected time interval, and a signal connector to allow transfer of signals, which are representative of the collected data, from the electronic memory to a remote communication unit in communication with the signal connector; and the method further including the step of removing said sterilant monitoring assembly from said apparatus after said selected time interval, the transferring step including transferring the collected data to the processor as signals transferred through the signal connector from said electronic memory to the remote communication unit after the sterilant monitoring assembly has been removed from the apparatus.

3. A method of monitoring sterilant in accordance with claim 2, wherein the data collection circuit is configured to perform data collection in accordance with selected conditions, the data collection circuit including a signal connector to allow entry of selected conditions for such data collection; the method further including the step of entering selected conditions for such data collection.

4. A method of monitoring sterilant in accordance with claim 1, wherein:

the sterilant monitoring assembly provided by the providing step further includes a temperature sensor operatively coupled to the data collection circuit to provide output signals corresponding to the ambient temperature proximate the sterilant sensor for collection in combination with the output signals from said sterilant sensor; and wherein the transferring step further includes transferring collected data from the data collection circuit representative of the detected ambient temperature to the processor.

5. A method of monitoring sterilant in accordance with claim 1, wherein:

the data collection circuit of the sterilant monitoring assembly provided by the providing step further includes a transmitter to transmit signals representative of the collected data to a remote communication unit in communication with the processor; and further wherein the transferring step includes transmitting collected data from the data collection circuit to the processor as signals transmitted through the transmitter.

6. A method of monitoring sterilant in accordance with claim 1, wherein:

the positioning step includes providing a carrier element configured as an article to be sterilized by the sterilization apparatus, said portable structure being placed on said carrier element; and loading the carrier element on the conveyor path as an article to be sterilized by the sterilization apparatus.

7. A method of monitoring sterilant in accordance with claim 1, wherein:

said sterilant includes hydrogen peroxide ($H_2O_2$) vapor, said sterilant sensor providing output signals corresponding to detected levels of the $H_2O_2$ vapor.

8. A method of monitoring sterilant in accordance with claim 1, wherein:

the positioning step includes providing a carrier element configured as an article to be sterilized by the sterilization apparatus, said portable structure being placed inside said carrier element; and loading the carrier element on the conveyor path as an article to be sterilized by the sterilization apparatus.

\* \* \* \* \*